United States Patent [19]
Evers et al.

[11] 3,989,856
[45] *Nov. 2, 1976

[54] 3-FURYL BETA-OXOALKYL SULFIDES AND METHODS FOR USING SAME FOR ALTERING, MODIFYING OR ENHANCING THE ORGANOLEPTIC PROPERTIES OF FOODSTUFFS

[75] Inventors: William J. Evers, Red Bank; Howard H. Heinsohn, Jr., Hazlet; Christopher Giacino, Califon, all of N.J.

[73] Assignee: International Flavors & Fragrances Inc., New York, N.Y.

[ * ] Notice: The portion of the term of this patent subsequent to Oct. 12, 1993, has been disclaimed.

[22] Filed: Nov. 20, 1975

[21] Appl. No.: 633,791

Related U.S. Application Data

[63] Continuation-in-part of Ser. No. 581,894, May 29, 1975.

[52] U.S. Cl. .............................. 426/535; 260/347.2
[51] Int. Cl.$^2$ .......................................... A23L 1/231
[58] Field of Search .................... 260/347.2; 426/535

[56] References Cited
UNITED STATES PATENTS

| | | | |
|---|---|---|---|
| 3,666,495 | 5/1972 | Evers et al. | 426/535 |
| 3,872,111 | 3/1975 | Evers et al. | 260/347.2 |
| 3,873,731 | 3/1975 | Evers et al. | 426/535 |
| 3,891,710 | 6/1975 | Evers et al. | 260/347.2 |
| 3,910,966 | 10/1975 | Evers et al. | 260/347.2 |
| 3,917,869 | 11/1975 | Evers et al. | 426/535 |

*Primary Examiner*—Joseph M. Golian
*Attorney, Agent, or Firm*—Arthur L. Liberman; Harold Haidt; Franklin D. Wolffe

[57] ABSTRACT

3-Furyl beta-oxoalkyl sulfides having the structure:

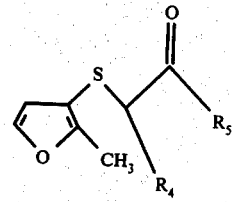

wherein $R_4$ is $C_3$ alkyl and $R_5$ is $C_4$ alkyl with $R_4$ being 2-propyl when $R_5$ is 2-methyl-1-propyl; and $R_4$ being 1-propyl when $R_5$ is 1-butyl, such 3-furyl beta-oxoalkyl sulfides taken alone or in admixture being useful in altering or modifying or enhancing the organoleptic properties of foodstuffs, foodstuffs containing same, and foodstuff flavoring compositions containing such 3-furyl beta-oxoalkyl sulfides.

12 Claims, 3 Drawing Figures

EXAMPLE I

EXAMPLE I

EXAMPLE IV

3-FURYL BETA-OXOALKYL SULFIDES AND METHODS FOR USING SAME FOR ALTERING, MODIFYING OR ENHANCING THE ORGANOLEPTIC PROPERTIES OF FOODSTUFFS

This application is a continuation-in-part of U.S. Application for letters patent Ser. No. 581,894, filed on May 29, 1975.

BACKGROUND OF THE INVENTION

The present invention relates to novel 3-furyl betaoxoalkyl sulfides.

Artificial flavoring agents for foodstuffs have received increasing attention in recent years. In many areas, such food flavoring agents are preferred over natural flavoring agents at least in part because of the uniform flavor that may be so obtained. For example, natural food flavoring agents such as extracts, essences, concentrates and the like are often subject to wide variaton due to changes in the quality, type and treatment of the raw materials. Such variation can be reflected in the end product and results in unreliable flavor characteristics and uncertainty as to consumer acceptance and cost. Additionally, the presence of the natural product in the ultimate food may be undesirable because of increased tendency to spoil. This is particularly troublesome in convenience and snack food usage where such products as dips, soups, chips, prepared dinners, canned foods, sauces, gravies and the like are apt to be stored by the consumer for some time prior to use.

The fundamental problem in preparing artificial flavoring agents is that of achieving as nearly as possible a true flavor reproduction. This generally proves to be a difficult task since the mechanism for flavoring development in many foods is not understood. This is noteable in products having sweet, meaty and roasted meat flavor and nut-like flavor characteristics. It is also noteable in products having vegetable-like and hydrolyzed vegetable protein-like and anise-like flavor characteristics.

Reproduction of roasted, beef brothy, nutty, citrus and fresh lime, and sweet, meaty flavors and aromas and hydrolyzed vegetable protein-like flavors and aromas has been the subject of the long and continuing search by those engaged in the production of foodstuffs. The severe shortage of foods, especially protein foods, in many parts of the world has given rise to the need for utilizing non-meat sources of proteins and making such proteins a palatable and as meat-like as possible. Hence, materials which will closely simulate or exactly reproduce the flavor and aroma of roasted meat and sweet, meat products, vegetable products and products having nut-like taste are required.

Moreover, there are a great many meat containing or meat based foods presently distributed in a preserved form. Examples being condensed soups, dry-soup mixes, dry meat, freeze-dried or lyophilized meats, packaged gravies and the like. While these products contain meat or meat extracts, the fragrance, taste and other organoleptic factors are very often impaired by the processing operation and it is desirable to supplement or enhance the flavors of these preserved foods with versatile materials which have either roasted meat or sweet meat or vegetable-like or nut-like nuances.

U.S. Pat. No. 3,666,594 provided materials having such desirable meat, roast meat and roasted fragrance and flavor notes. Such materials are organic oxygen containing heterocyclics wherein the second carbon atom from the oxygen atom contains a sulfur substituent and included 3-thia furan compounds having the structure:

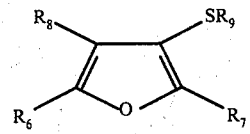

wherein $R_6$, $R_7$, $R_8$ and $R_9$ are the same or different alkyl or hydrogen. The process disclosed in this patent indicated that such furan 3-thiols and alkyl substituted furan 3-thiols can be produced by the reaction of an appropriate dihydrogen furanone-3 or tetrahydro furanone-3 with hydrogen sulfide in the presence of anhydrous hydrogen chloride at temperatures of $-60°$ to $-100°$ C.

Nothing in the prior art, however, sets forth implicitly or explicitly the 3-furyl beta-oxoalkyl sulfides of our invention and their unique and advantageous and unobvious flavor properties.

U.S. application for Pat. Ser. No. 542,830, filed on Jan. 21, 1975, discloses the use in meat flavors of 3-furyl beta oxoalkyl sulfides having the structure:

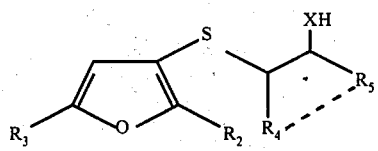

where X is a chalcogen selected from the group consisting of oxygen and sulfur; $R_2$ and $R_3$ are each selected from the group consisting of methyl and hydrogen, at least one of $R_2$ or $R_3$ being methyl; and $R_4$ and $R_5$, taken separately, are each methyl, or $R_4$ and $R_5$ taken together are tetramethylene.

Figure 1:
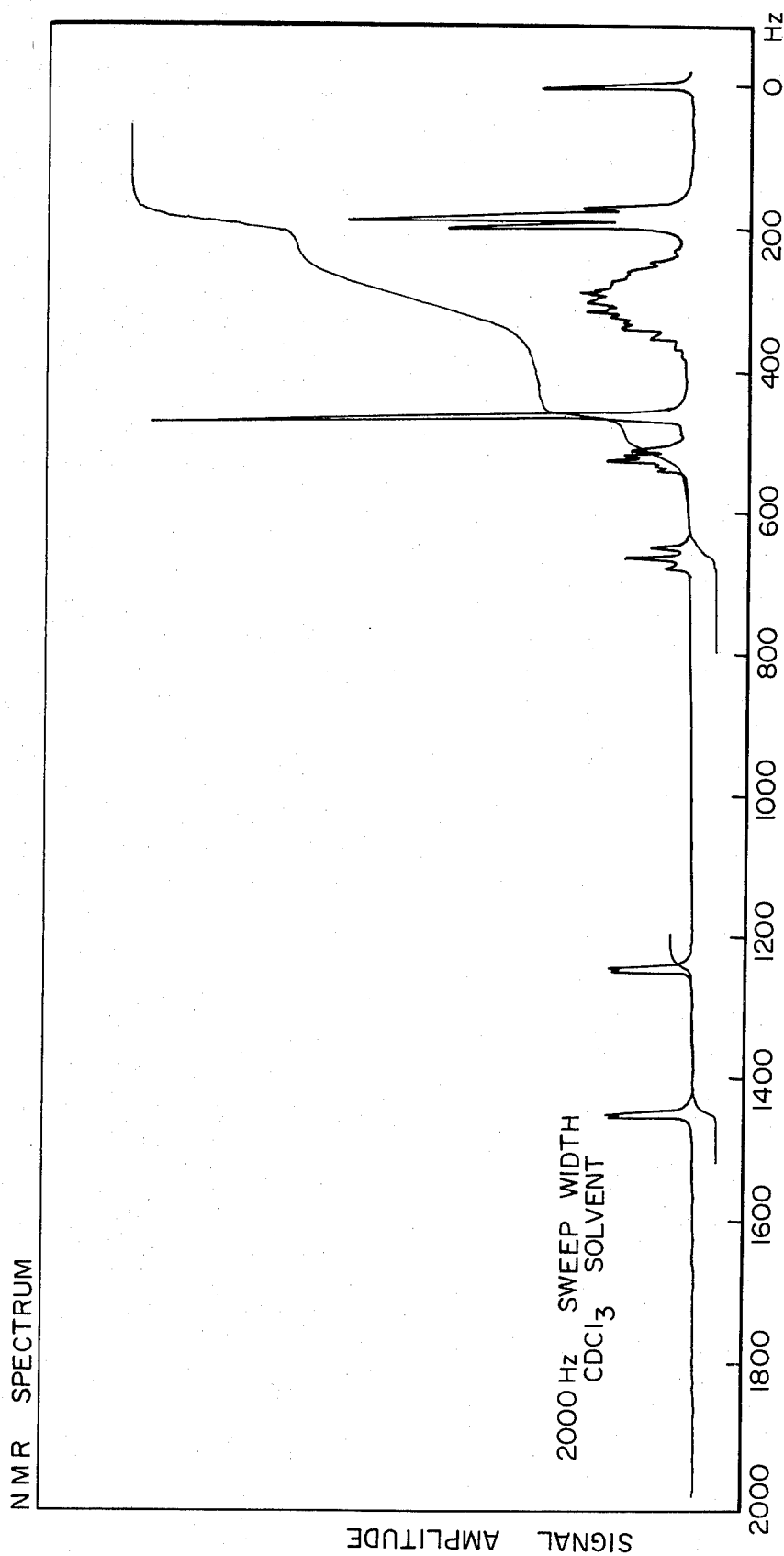
FIG. 1 is the NMR spectrum for the product of Example I, wherein (1,3-di-n-propylacetonyl)(2-methyl-3-furyl) sulfide is produced.

The present invention provides novel 3-furyl beta-oxoalkyl sulfides useful for altering, modifying or enhancing the organoleptic properties of foodstuffs, as well as methods for altering or enhancing or modifying the organoleptic properties, e.g. taste and aroma, of said foodstuffs.

The novel compounds of our invention are 3-furyl beta-oxoalkyl sulfides having the structure:

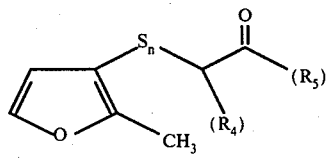

wherein $R_4$ is $C_3$ alkyl and $R_5$ is $C_4$ alkyl with $R_4$ being 2-propyl when $R_5$ is 2-methyl-1-propyl and $R_4$ being 1-propyl when $R_5$ is 1-butyl.

Thus, the 3-furyl beta-oxoalkyl sulfides contemplated within the scope of our invention are, for example:

| 3-Furyl-beta-oxoalkyl sulfide compound | Structure |
|---|---|
| (1,3-di-n-propylacetonyl) (2-methyl-3-furyl) sulfide | 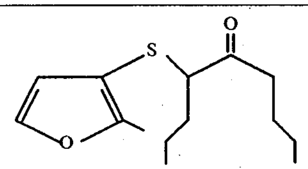 |
| (1,3-diisopropylacetonyl) (2-methyl-3-furyl) sulfide | 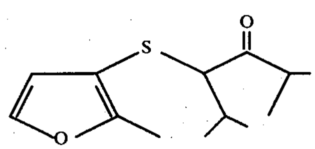 |

The 3-furyl beta-oxoalkyl sulfides of our invention may be produced according to a process which comprises the steps of:
i. Carrying out a reaction of a 3-mercapto furan with an oxo-α-haloalkane (alternatively named: alpha-haloalkanone) to form the compounds of our invention according to the following reaction:

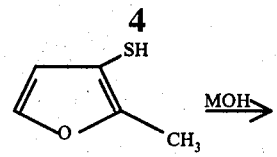

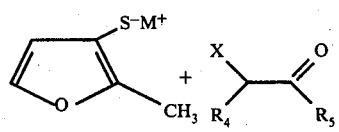

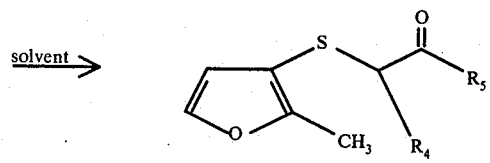

ii. Physically separating said 3-furyl beta-oxoalkyl sulfides from the reaction mass;
wherein X is a halogen selected from the group consisting of chloro and bromo; wherein $R_4$ and $R_5$ are as defined above, and wherein M is an alkali metal.

The following table sets forth examples of specific reactants and the resulting products produced using the process of our invention:

TABLE I

| Oxo-alpha-halo alkane or cycloalkane or bicycloalkane reactant | 3-furan-thiol reactant | 3-furyl-beta-oxoalkyl sulfide compound | Structure |
|---|---|---|---|
| 4-chloro-5-nonanone | 2-methyl-3-furan thiol | (1,3-di-n-propyl-acetonyl)(2-methyl-3-furyl) sulfide | 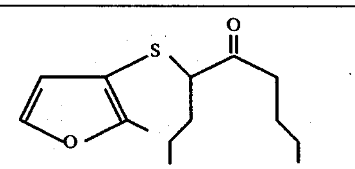 |
| 2,6-dimethyl-3-chloro-hexan-4-one | 2-methyl-3-furan thiol | (1,3-diisopropyl) (2-methyl-3-furyl) sulfide | 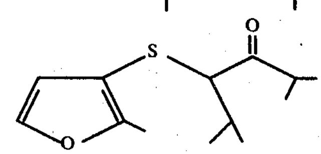 |

This reaction of our invention, in order to proceed in a practical manner, takes place using an alkali metal salt of a 3-furan thiol, such as the sodium or potassium salt of 2-methyl-3-furan thiol. The alpha haloalkanone may be a bromo derivative or a chloro derivative. Each of the reactants is preferably dissolved in an appropriate inner reaction solvent, e.g. methanol.

Other solvents which are non-reactive, which may be used in carrying out this reaction, are ethanol or isopropanol.

The mole ratio of the reactants, the alkali metal salt of the 3-furan thiol:alpha haloalkanone may vary from 1:1 up to 5:1, with a preferred ratio of alkali metal salt of 3-furan thiol:alpha haloalkanone of 1:1.

The reaction temperature may vary from about 10° C up to about 40° C with a preferred temperature of 25° C. The time of reaction is a function of the reaction temperature with lower reaction temperatures giving rise to longer periods of time of reaction and higher temperatures of reaction giving rise to much shorter periods of time of reaction. However, at the upper limits of the reaction temperature range, the yield of product is lower due to increased quantities of by-product being formed.

The reaction is preferably carried out at atmospheric pressure, but pressures greater than atmospheric, e.g. 5 atmospheres may be used without detrimentally affecting the yield of product or the time of reaction which is required to obtain such yield.

At the end of the reaction, the reaction product is extracted from the reaction mass using a non-reactive solvent, e.g. n-hexane or methylene dichloride, after the reaction mass is first quenched with water and neutralized with aqueous acid. The solvent extract is then dried, concentrated and distilled preferably by means of vacuum distillation.

The 3-furyl beta-oxoalkyl sulfides of our invention, produced as stated above, have useful organoleptic properties giving rise to the use as foodstuffs flavors or flavor adjuvants or flavor enhancers as set forth in an illustrative manner as set forth in the following Table II:

The term "enhances" is intended to be used herein to mean "the intensification of a flavor or aroma characteristic, note or nuance without the modification by the enhancement agent of the quality of said characteristic, note or nuance." Thus "enhancement" of a flavor or aroma of a flavor composition or of a foodstuff means that the ehnahcement agent does not add or subtract any particular flavor note or nuance to or from the organoleptic impression of said flavor composition or of said foodstuff.

Such 3-furyl beta-oxalkyl sulfides are accordingly useful in flavoring compositions. Flavoring compositions are herein taken to mean those which contribute a part of the overall flavor impression by supplementing or fortifying a natural or artificial flavor in a material, as well as those which supply substantially all the flavor and/or aroma character to a consumable article.

The term "foodstuff" as used herein includes both solid and liquid ingestible materials for man or animals, which materials usually do, but need not, have nutritional value. Thus, foodstuffs includes meats, gravies, soups, convenience foods, malt and other alcoholic or non-alcoholic beverages, milk and dairy products, nut butters such as peanut butter and other spreads, seafoods including fish, crustaceans, mollusks and the like, candies, breakfast foods, baked goods, vegetable, cereals, soft drinks, snack foods, dog and cat foods, other veterinary products, and the like.

When the 3-furyl beta-oxoalkyl sulfides according to this invention are used in a food flavoring composition, they can be combined with conventional flavoring materials or adjuvants. Such co-ingredients or flavoring adjuvants are well known in the art for such use and have been extensively described in the literature. The requirements of such adjuvant materials are that (i)

TABLE II

| 3-Furyl beta-Oxoalkyl Sulfide Compound | Structure | Flavor Properties |
| --- | --- | --- |
| (1,3-di-n-propyl-acetonyl)(2-methyl-3-furyl) sulfide | 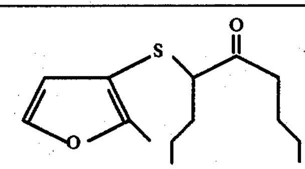 | Meaty/sweet, beefy broth and meaty, roasted aroma and meaty/sweet, beef broth flavor with bloody nuance and meaty aftertaste |
| (1,3-diisopropyl-acetonyl)(2-methyl-3-furyl) sulfide | 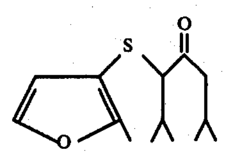 | Sweet, roasted meat aroma and sweet, roasted meat and citrus flavor with onion nuances. |

Thus, the 3-furyl beta-oxoalkyl sulfides produced according to the instant invention can be used to alter, vary, fortify, modify, enhance or otherwise improve the oganoleptic properties, including flavor and/or aroma, of a wide variety of materials which are ingested, consumed, or otherwise organoleptically sensed.

The terms "alter" and "modify" in their various forms will be understood herein to mean the supplying or imparting a flavor character or note to an otherwise bland, relatively tasteless substance, or augmenting an existing flavor characteristic where the natural flavor is deficient in some regard, or supplementing the existing flavor or aroma impression to modify the organoleptic character. The materials which are so altered are generally referred to herein as consumable materials.

they be non-reactive with the 3-furyl beta-oxoalkyl sulfides of our invention; (ii) that they be organoleptically compatible with the 3-furyl beta-oxoalkyl monosulfides of our invention whereby addition of the said adjuvant(s) does not give rise to any diminution of the desired nuances or has a deleterious effect on said desired nuances; (iii) in conjunction with the 3-furyl beta-oxoalkyl monosulfides of our invention, the organoleptic impression created or enhanced by the 3-furyl beta-oxoalkyl monosulfides not be detrimentally impaired; (iv) that they be ingestibly acceptable from an organoleptic standpoint; (v) and that they be non-toxic or otherwise non-deleterious.

Apart from these requirements, convention materials can be used and broadly include other flavor materials, vehicles, stabilizers, thickeners, surface active agents, conditioners and flavor intensifiers.

Examples of preferred co-flavoring adjuvants are:
Methyl thiazole alcohole (4-methyl-5-beta-hydroxyethyl thiazole);
2-Methyl butanethiol;
4-mercapto- 2-butanone;
3-Mercapto-4-pentanone;
1-Mercapto-2-propanone;
Benzaldehyde;
Furfural;
Furfural alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;
2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;
Hydrolyzed vegetable protein;
2-Methylfuran-3-thiol;
2-Methyldihydrofuran-3-thiol;
2,5-Dimethylfuran-3-thiol;
Hydrolyzed fish protein; and
Tetramethyl pyrazine The 3-furyl beta-oxoalkyl sulfides or the compositions incorporating them, as mentioned above, can be combined with one or more vehicles or carriers for adding them to the particular product. Vehicles can be edible or otherwise suitable materials such as ethyl alcohol, propylene glycol, water and the like. Carriers include materials such as gum arabic, carrageenan, other gums and the like. The 3-furyl beta-oxoalkyl sulfides according to this invention can be incorporated with the carriers by conventional means such as spray-drying, drum-drying and the like. Such carriers can also include materials for coacervating the 3-furyl beta-oxoalkyl sulfides (and other flavoring ingredients, as present) to provide encapsulated products. When the carrier in an emulsion the flavoring composition can also contain emulsifiers such as mono- and diglycerides or fatty acids and the like. With these carriers or vehicles, the desired physical form of the composition can be prepared.

The quantity of 3-furyl beta-oxoalkyl sulfides utilized should be sufficient to impart the desired flavor characteristic to the product, but on the other hand, the use of an excessive amount of the derivative is not only wasteful and uneconomical, but in some instances too large a quantity may unbalance the flavor or other organoleptic properties of the product consumed. The quantity used will vary depending upon the ultimate foodstuff; the amount and type of flavor initially present in the foodtuff; the further process or treatment steps to which the foodstuff will be subjected; regional and other preference factors; the type of storage; if any, to which the product will be subjected; and the preconsumption treatment, such as baking, frying, and so on, given to the product by the ultimate consumer. Accordingly, the terminology "effect amount" and "sufficient amount" is understood in the context of the present invention to be quantitatively adequate to alter the flavor of the foodstuff.

It is accordingly preferred that the ultimate compositions contain from about 0.005 parts per million (ppm) to about 250 ppm of 3-furyl beta-oxoalkyl sulfides or mixtures thereof. More particularly, in food compositions it is desirable to use from about 0.01 ppm for enhancing flavors and in certain preferred embodiments of the invention, from about 0.01 to 50 ppm of the drivatives are included to add positive flavors to the finished product.

The amount of 3-furyl beta-oxoalkyl sulfides or mixtures thereof of our invention to be utilized in flavoring compositions can be varied over a wide range depending upon the particular quality to be added to the foodstuff. Thus, amounts of one or more derivatives according to the present invention of from about 0.5 ppm up to 80 or 90 percent of the total flavoring composition can be incorporated in such compositions. It is generally found to be desirable to include from about 1 ppm up to about 0.1 percent of the 3-furyl beta-oxalkyl sulfides in such compositions.

The following examples are given to illustrate embodiment of the invention as it is preferably preferred to practice it. It will be understood that these examples are illustrative and the invention is not to be considered as restricted thereto except as indicated in the appended claims.

All parts, proportions, percentages, and ratios herein are by weight unless otherwise indicated.

EXAMPLE I

PREPARATION OF
(1,3-DI-n-PROPYLACETONYL)(2-METHYL-3-FURYL) SULFIDE

Part A
Reaction:

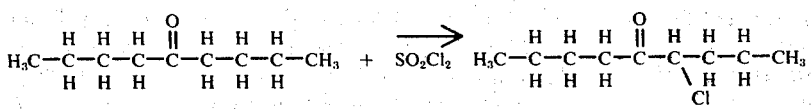

Into a 250 ml 3 neck round bottom flask equipped with magnetic stirrer, 50 ml addition funnel, pot thermometer and reflux condenser (with vacuum outlet to water aspirator) and cold water bath, 81 g of di-n-butyl ketone is placed. Over a period of 1 hour with external cooling being applied, 12 cc (20.3 g; 0.15 moles) of SO$_2$Cl$_2$ is added while removing the acidic gases, hydrogen chloride and sulfur dioxide using the water aspirator. After the 1 hour period, full vacuum is applied with stirring continuing for another 1½ hours. The reaction mass is then transferred to a 250 ml one neck round bottom flask to which vacuum is applied using a water aspirator at room temperature. The resulting crude oil weighing 75.0 g is then removed from the flask for distillation. The 4-chloro-5-nonanone reaction product is then distilled.

Part B
Reaction:

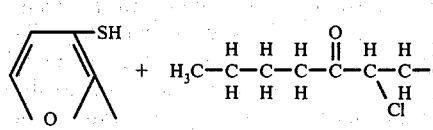

Into a 25 ml, round bottom, 3 necked flask equipped with magnetic stirrer, Y-tube, nitrogen inlet tube, thermometer and cold water bath, the following materials are placed:
  i. 2-methyl-3-furan thiol; 0.57 g (3 cc; 0.005 moles);
  ii. solution of sodium methoxide in methanol (weight 0.27 g[3 cc; 0.005 moles])

1.17 g of 75.6% (1 cc; 0.005 moles) 4-chlorio-5-nonanone (prepared in Part A) in absolute methanol is then slowly added to the reaction mass with stirring while maintaining the reaction mass at 25°–35° C. The reaction mass is then stirred at 25° C under a nitrogen blanket for a period of 15 hours. At the end of the 15-hour period, the reaction mass is sampled and analyzed using GLC analysis (8' by ½' column coated with SE-30, operated at 130°1 C, programmed at 7.5° C/minute).

The reaction mass is then concentrated using a water aspirator vacuum on a rotary evaporator, thus forming a white slurry, having a volume of 4–5 ml. 10 ml Water is then added to the white slurry with stirring, and the solid dissolves. At this point the pH of the resulting material is between 6 and 7. The resulting mixture now exists in two phases; an oil phase and an aqueous phase. The oil phase is extracted with three 5-ml portions of n-hexane and the hexane extracts are combined and washed with saturated sodium chloride solution. The hexane extract is then dried over anhydrous sodium sulfate, gravity filtered and concentrated on a rotary evaporator yielding product weighing 1.4 grams. GLC analysis (8' × ¼" column coated with SE-30; operated at 130° C, programmed at 7.5° C/minute) indicates the following:
  65.2% product
  10.9% 4-chloro-5-nonanone 16.0% 5-nonane
0.3% 2-methyl-3-furan thiol
3.4% solvent NMR, IR, and Mass Spectral analysis confirm that the product has the structure:

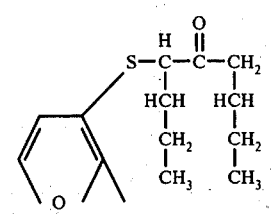

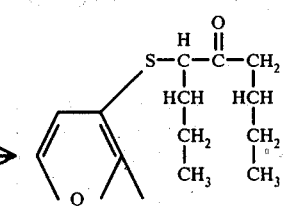

Mass spectral analysis is as follows:

| m/e ratio | Relative Intensity |
|---|---|
| 29 | 15 |
| 41 | 22 |
| 43 | 15 |
| 55 | 23 |
| 57 | 34[4] |
| 87 | 28[6] |
| 113 | 78[2] |
| 127 | 29[5] |
| 169 | 100[1] |
| M254 | 42[3] |

The NMR Analysis is as follows:

| Peak | Interpretation | |
|---|---|---|
| 0.92 (t) | CH$_3$—CH$_2$— | 6 H |
| 1.52 (m) | —CH$_2$— | 8 H |
| 2.31 (s) | CH$_3$ \| —O—C=C | 3 H |
| 2.60 (m) | CH$_2$—C— \|\| O | 2 H |
| 3.32 (t) | O \|\| —S—CH—C— | 1 H |
| 6.23 (d, J = 2Hz) | | 1 H |
| 7.26 (d, J = 2Hz) | | 1 H |

Figure 2:
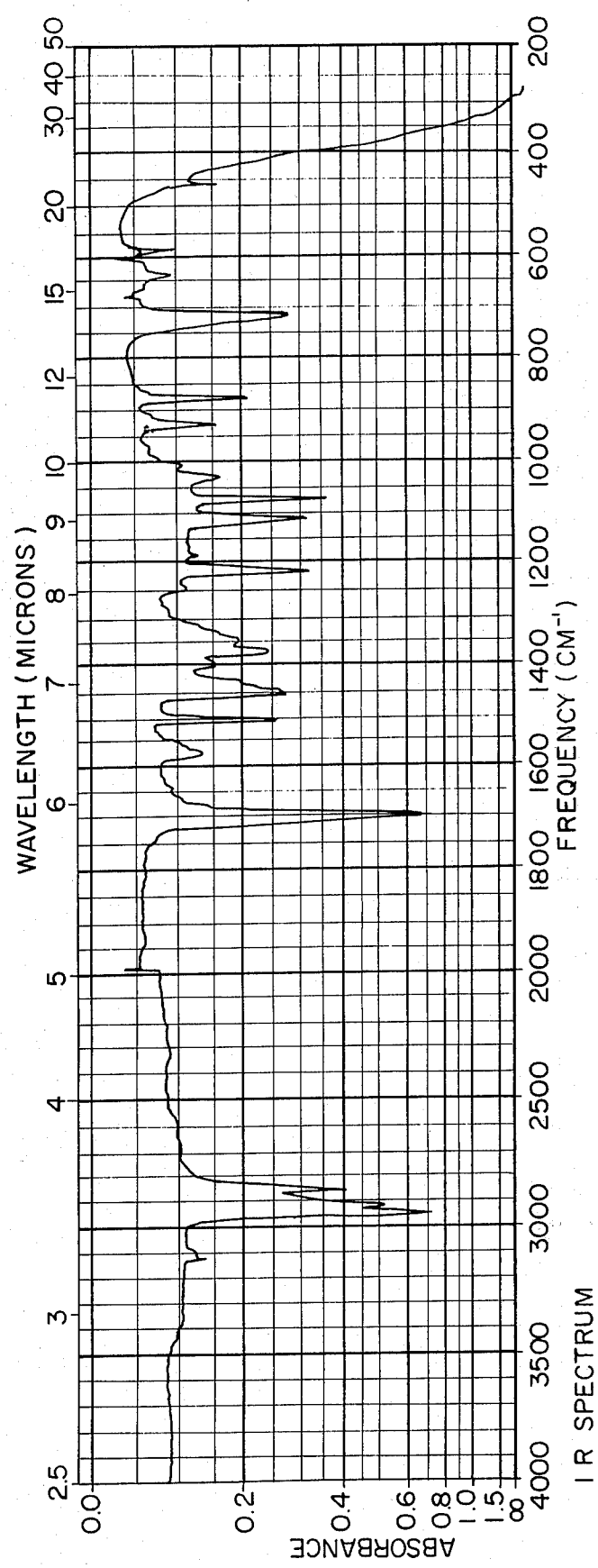
FIG. 2 is the IR spectrum for the product of Example I, wherein (1,3-di-n-propylacetonyl)(2-methyl-3-furyl) sulfide is produced.

The NMR spectrum is set forth in FIG. 1. The Infrared analysis is as follows: 715, 1075, 1115, 1215, 1445, 1455, 1695, 2860, 2920, 2940 cm$^{-1}$ The infrared spectrum is set forth in FIG. 2.

The resulting product has a meaty/sweet, beef broth-like and meaty roasted aroma characteristic and a meaty/sweet, beef broth flavor characteristic with a meaty aftertaste and a bloody nuance.

EXAMPLE II

The (1,3-di-n-propylacetonyl)(2-methyl-3-furyl) sulfide prepared in Example I is dissolved in propylene glycol to provide a 0.1% solution. This solution in the amount of 0.9 g is added to 7.3 g of a soup base consisting of:

| Ingredient | Parts by Weight |
|---|---|
| Fine ground sodium chloride | 35.5 |
| Hydrolyzed vegetable protein | 27.5 |
| Monosodium glutamate | 18.0 |
| Sucrose | 11.0 |
| Beef fat | 5.5 |
| Sethness caramel color (powder B & C) | 2.7 |

The resulting mixture has a meaty/sweet, meaty roasted aroma and a meaty/sweet flavor character with intensified natural beef broth and bloody nuances and a meaty aftertaste.

EXAMPLE III (1,3-di-n-propylacetonyl)(2-methyl-3-furyl) sulfide prepared according to the process of Example I is added to a 2% solution of Wyler's "Beef Flavored Instant Bouillon" (manfactured by Wyler Foods, Division of Bordon, Inc., Chicago, Ill.,), (Ingredients: salt, hyrolyzed vegetable protein, malto dextrin, sugar beef fat, water, monosodium glutamate, flavorings, corn sugar, beef extract, caramel color, hydrogenated vegetable fat and U.S. certified food color)

at the rate of 1 ppm. The resulting beef flavored bouillon has a meaty/sweet and meaty/roasted aroma with a meaty/sweet flavor characteristic and a meaty aftertaste and bloody nuance.

EXAMPLE IV

PREPARATION OF (1,3-DIISOPROPYLACETONYL)(2-METHYL-3-FURYL) SULFIDE

Reaction:

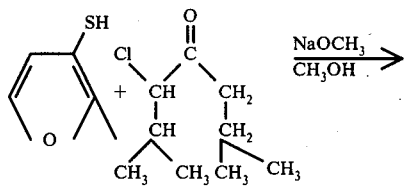

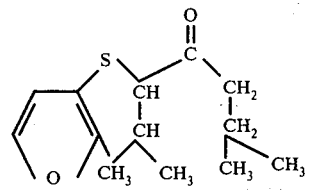

Into a 25 ml, round-bottom, 3-necked flask equipped with magnetic stirrer, "Y" tube, nitrogen inlet, cold water bath, reflux condenser and thermometer is placed a solution of 0.41 g (0.00755 moles) of sodium methoxide dissolved in 4.5 ml absolute methanol. The sodium methoxide solution is cooled using a water bath to 23° C. A solution of 0.86 g. (0.00755 moles) of 2-methyl-3-furan thiol is 4.5 ml absolute methanol is then added to the sodium methoxide solution dropwise from a pipette while maintaining the temperature of the reaction mass between 25° C and 28° C. While maintaining the temperature of the reaction mass at 25°–28° C, 2,6-dimethyl-3-chloroheptanone-4 (1.37 g, 0.00755 moles) in 1.5 ml absolute methanol is added dropwise. A white solid precipitate forms. The reaction mass is then stirred for a period of 1 hour while maintaining the temperature at 25°–28° C. After this 1-hour period, a sample is removed from the reaction mass and to it water is added, and the pH is adjusted to 3–4 with 10% HCl. The sample then exists in two phases, an oil phase and an aqueous phase. The oil phase is extracted with hexane, and the hexane extract is dried, concentrated and analyzed using GLC analysis (8' × ¼'' SE-30 coated column; operated at 130° C, programmed at 7.5°/minute) indicating approximately 50–60% product.

At this point the reaction mass is concentrated using water aspirator vacuum on a rotary evaporator. The resulting material is a white slurry having a volume of approximately 5 ml. 15 ml of water is added to this slurry with stirring and the solid dissolves, with an oil phase separating out. At this point the pH of the solution is 9–10. The resulting mixture is neutralized to a pH of about 4–5 using 20 drops of 10% aqueous hydrochloric acid. The oil phase is extracted with two 12 ml portions of n-hexane, and the extracts are combined and washed with 5 ml saturated sodium chloride and dried over anhydrous sodium sulfate and gravity filtered. The filtrate is then concentrated on a rotary evaporator to yield a product within 1.4 grams. GLC analysis (conditions: 8' × ¼'' column coated with SE-30, operated at 130° C, programmed at 10° C/minute) indicates the following materials present:

| | |
|---|---|
| 2-methyl-3-furan thiol | 2.2% |
| 2,6-dimethyl-3-chloro-4-heptanone | 10.5% |
| bis(2-methyl-3-furyl)disulfide | 3.4% |
| the product, 1,3-diisopropyl-acetonyl)(2-methyl-3-furyl) sulfide | 64.5% |

Mass spectral analysis is as follows:

| m/e | Relative Intensity |
|---|---|
| 41 | 26[6] |
| 43 | 24 |
| 55 | 18 |
| 57 | 37[5] |
| 85 | 23 |
| 87 | 53[3] |
| 95 | 14 |
| 113 | 95[2] |
| 169 | 100[1] |
| M254 | 40[4] |

Figure 3:
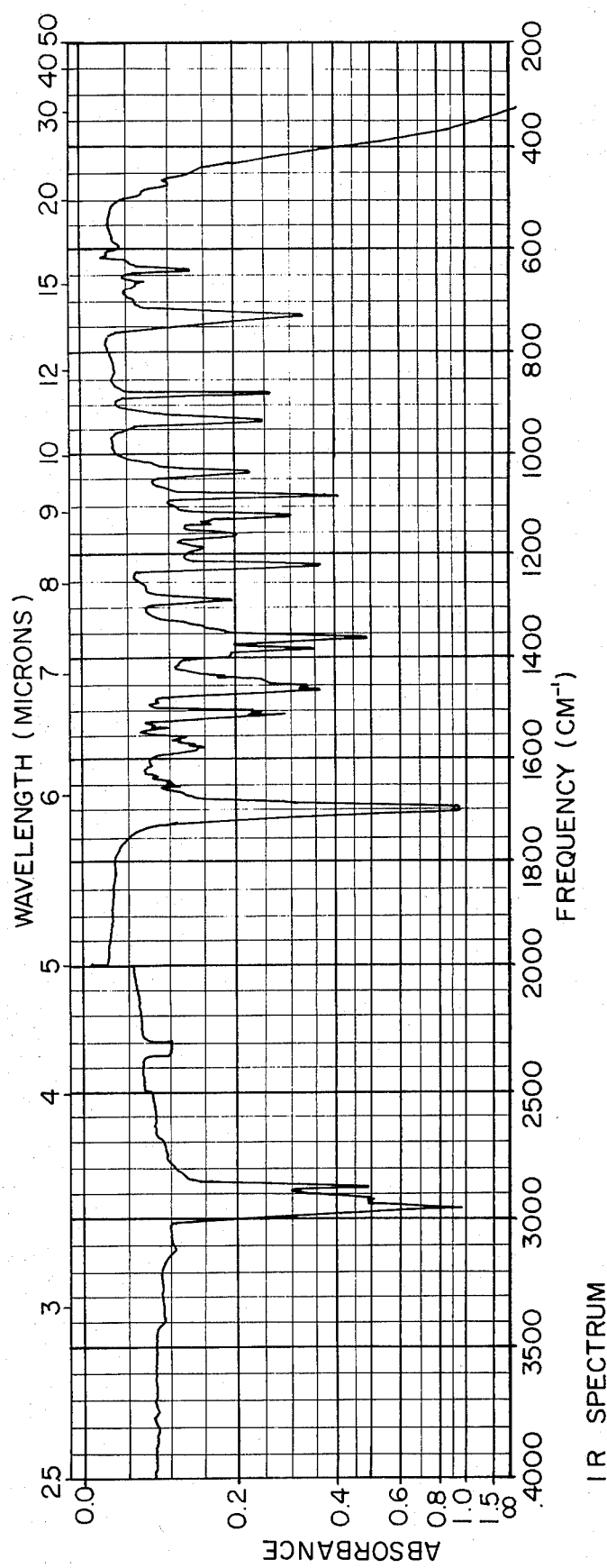
FIG. 3 is the IR spectrum for the product of Example IV, wherein (1,3-diisopropylacetonyl)(2-methyl-3-furyl) sulfide is poduced.

The infrared analysis is as follows: 725, 885, 930, 1085, 1120, 1220, 1360, 1380, 1450, 1460, 1510, 1700, 2870, 2920, 2960 cm$^{-1}$ The infrared spectrum is set forth in FIG. 3.

GLC, NMR, IR and Mass Spectral analyses yields the information that this material has the structure:

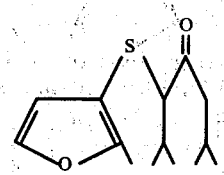

The resultant material has a sweet, roasted meat (beef) citrus and fresh lime aromas and flavor with onion nuances.

EXAMPLE V (1,3-diisopropylacetonyl)(2-methyl-3-furyl) sulfide, prepared according to the process of Example IV, is added to a 2% solution of Wyler's "Beef Flavored Instant Bouillon" (manufactured by Wyler Foods, Division of Borden, Inc., Chicago, Ill.), (Ingredients: salt, hydrolyzed vegetable protein, malto dextrin, sugar, beef fat, water, monosodium glutamate, flavorings, corn sugar, beef extract, caramel color, hydrogenated vegetable fat and U.S. certified food color)

at the rate of 0.1 ppm. This chemical adds sweet, roast beef, citrus and fresh lime characteristic with an oniony nuance to the beef broth.

What is claimed is:

1. A 3-furyl beta-oxoalkyl sulfide having the structure:

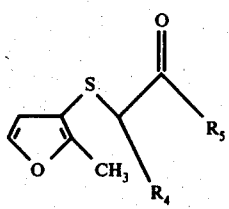

wherein $R_4$ is $C_3$ alkyl and $R_5$ is $C_4$ alkyl, $R_4$ being 2-propyl when $R_5$ is 2-methyl-1-propyl and $R_4$ being 1-propyl when $R_5$ is 1-butyl.

2. The 3-furyl beta-oxoalkyl sulfide compound of claim 1 wherein $R_4$ is 2-propyl and $R_5$ is 2-methyl-1-propyl having the structure:

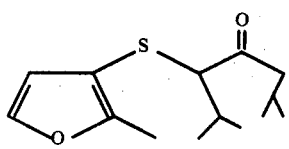

3. The 3-beta-oxoalkyl sulfide compound of claim 1 when $R_4$ is 1-propyl and $R_5$ is 1-butyl, having the structure:

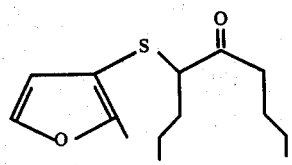

4. A process for augmenting or enhancing the meaty flavor of a foodstuff comprising the step of adding to said foodstuff from about 0.005 parts per million up to about 250 parts per million of a 3-furyl beta-oxoalkyl sulfide compound as defined in claim 1.

5. The process of claim 4 wherein the structure of the 3-furyl beta-oxoalkyl sulfide compound is:

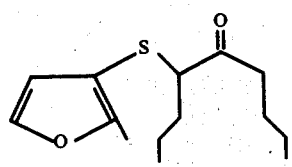

6. The process of claim 4 wherein the structure of the 3-furyl beta-oxoalkyl sulfide compound is:

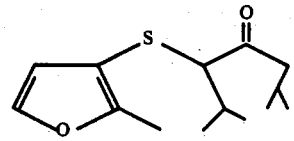

7. A composition for augmenting or enhancing the meaty flavor of a foodstuff comprising (i) from about 0.5 ppm up to 90 percent of a 3-furyl beta-oxoalkyl sulfide as defined in claim 1; the remainder of said composition being (ii) at least one flavoring adjuvant which is non-reactive with said 3-furyl beta-oxoalkyl sulfide and which is organoleptically compatible with said 3-furyl beta-oxoalkyl sulfide, and which is selected from the group consisting of:
4-methyl-5-beta hydroxyethyl thiazole;
2-methyl butanethiol;
4-Mercapto-2-butanone;
3-Mercapto-4-pentanone;
1-Mercapto-2-propanone;
Benzaldehyde;
Furfural;
Furfural alcohol;
2-Mercapto propionic acid;
Alkyl pyrazine;
Methyl pyrazine;
2-Ethyl-3-methyl pyrazine;
Tetramethyl pyrazine;
Polysulfides;
Dipropyl disulfide;
Methyl benzyl disulfide;
Alkyl thiophenes;

2-Butyl thiophene;
2,3-Dimethyl thiophene;
5-Methyl furfural;
Acetyl furan;
2,4-Decadienal;
Guiacol;
Phenyl acetaldehyde;
δ-Decalactone;
d-Limonene;
Acetoin;
Amyl acetate;
Maltol;
Ethyl butyrate;
Levulinic acid;
Piperonal;
Ethyl acetate;
n-Octanal;
n-Pentanal;
Hexanal;
Diacetyl;
Monosodium glutamate;
Sulfur-containing amino acids;
Cysteine;
Hydrolyzed vegetable protein;
2-Methylfuran-3-thiol;
2-Methyldihydrofuran-3-thiol;
2,5-Dimethylfuran-3-thiol;
Hydrolyzed fish protein; and
Tetramethyl pyrazine 8. The flavor composition of claim 7 wherein the structure of the 3-furyl beta-oxoalkyl sulfide is:

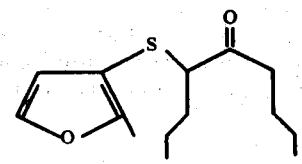

9. The flavor composition of claim 7 wherein the structure of the 3-furyl beta-oxoalkyl sulfide is:

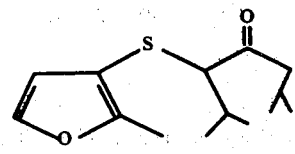

10. The composition of claim 7 wherein the quantity of 3-furyl beta-oxoalkyl sulfide is from about 1 ppm up to 0.1 percent.

11. The process of claim 4 wherein the quantity of 3-furyl beta-oxoalkyl sulfide is from 0.01 ppm up to 100 ppm.

12. The composition of claim 7 further including a carrier.

* * * * *

UNITED STATES PATENT AND TRADEMARK OFFICE
CERTIFICATE OF CORRECTION

PATENT NO. : 3,989,856
DATED : November 2, 1976
INVENTOR(S) : WILLIAM J. EVERS, HOWARD H. HEINSOHN, JR. AND CHRISTHOPHER GIACINO It is certified that error appears in the above-identified patent and that said Letters Patent are hereby corrected as shown below:

Col. 9, line 49, the number "130°IC" should read "130°C.

Col. 9, line 41, the word "4-chlorio-5-" should read "4-chloro-5-".

Signed and Sealed this

Seventeenth Day of May 1977

[SEAL]

Attest:

RUTH C. MASON
*Attesting Officer*

C. MARSHALL DANN
*Commissioner of Patents and Trademarks*